(12) United States Patent
Kuhn

(10) Patent No.: US 6,726,472 B2
(45) Date of Patent: Apr. 27, 2004

(54) ORTHODONTIC MEASUREMENT GAUGE

(76) Inventor: Robert J. Kuhn, 4090 Cuervo Ave., Santa Barbara, CA (US) 93110

( * ) Notice: Subject to any disclaimer, the term of this patent is extended or adjusted under 35 U.S.C. 154(b) by 0 days.

(21) Appl. No.: 10/055,531

(22) Filed: Jan. 22, 2002

(65) Prior Publication Data

US 2002/0098459 A1 Jul. 25, 2002

Related U.S. Application Data

(60) Provisional application No. 60/263,493, filed on Jan. 23, 2001.

(51) Int. Cl.$^7$ .................................................. A61C 3/00
(52) U.S. Cl. ............................. 433/3; 433/72; 533/514; 533/558.01
(58) Field of Search .................... 433/3, 72; 33/513, 33/514, 558.01

(56) References Cited

U.S. PATENT DOCUMENTS

| | | | |
|---|---|---|---|
| 797,559 A | * | 8/1905 | Cook |
| 3,871,098 A | * | 3/1975 | Dean |
| 3,906,634 A | * | 9/1975 | Aspel |
| 4,035,919 A | * | 7/1977 | Cusato |
| 4,725,228 A | * | 2/1988 | Andrews ........................ 433/3 |
| 4,768,953 A | * | 9/1988 | Nestor et al. ................. 433/72 |
| 4,822,277 A | * | 4/1989 | Nevell ............................ 433/3 |
| 6,296,482 B1 | * | 10/2001 | Kapit ............................ 433/3 |

* cited by examiner

*Primary Examiner*—Ralph A. Lewis
(74) *Attorney, Agent, or Firm*—Rodgers & Rodgers

(57) ABSTRACT

A gauge for measuring and/or marking teeth or models of teeth for the determination of the placement of attachments for orthodontic braces. The gauge has a first arm with a gauge element with a longitudinal extension portion lying on a first axis and a vertical extension portion extending generally perpendicularly from the first axis of the longitudinal extension portion. The gauge has a second arm which has a pointer or marking element at an end thereof, the pointer element having a tip which is spaced apart from the longitudinal extension portion of the first arm, the first and second arm being connected together to maintain the spaced apart relationship between the tip of marking element and the longitudinal extension portion with the vertical extension portion extending towards the pointer or marking element. The invention also provides a gauge element for converting a bow divider into a gauge for measuring and/or marking teeth for the determination of the placement of attachments for orthodontic braces. The gauge element has an elongate extension portion lying on a first axis and a vertical extension portion extending generally perpendicularly to the first axis of the elongate extension portion with the vertical extension portion extending outwardly between about 2.00 mm and 3.00 mm from the longitudinal extension portion.

23 Claims, 5 Drawing Sheets

ORTHODONTIC MEASUREMENT GAUGE

CROSS-REFERENCE TO RELATED APPLICATION(S)

This applications claims priority based upon provisional patent application No. 60/263,493, filed Jan. 23, 2001.

BACKGROUND OF THE INVENTION

The invention is in the field of measurement gauge that is used to assist in accurately placing the braces (individual attachments primarily composed of brackets and tubes) onto the upper and lower teeth on an orthodontic patient.

Presently, all measurement gauges used to position attachments on teeth function by making a linear measurement from the edges or cusp tips of all anterior (front) or posterior (back) teeth on the labial (lip) or buccal (cheek) side of the individual teeth toward the gingival (gum). This measurement is at a set distance from these landmarks i.e. cusp tips and biting edges of all teeth. Due to the anatomic variation in the height of cusps of posterior teeth, random wear patterns, and occasional cusp fractures, this method has numerous shortcomings in accuracy.

In reality, the orthodontist wants to position the attachments on all teeth so that the marginal ridges of the posterior teeth (the biting surface peripheral ridges located on the interproximal or side of the tooth) line up next to adjacent teeth in height. The marginal ridges should line up with little or no individual tooth marginal ridge variation in height to achieve the correct position of both upper and lower posterior teeth in order to allow opposing teeth to fit together when a person bites (or occludes) their teeth together.

The attachments on the posterior teeth should initially be positioned on each tooth so that when a straight wire (bent in the shape of an upper or lower dental arch of teeth) is engaged in the brackets and tubes, the teeth being adjusted will eventually be ideally aligned one to the other in either an upper or lower dental arch, and when the opposing teeth are brought together in a neutral bite, they occlude (fit together) ideally.

There accordingly remains a need for an accurate and easy to use gauge for measuring and/or marking teeth of an orthodontic patient for placement of braces thereon.

SUMMARY OF THE INVENTION

The invention provides a gauge that ideally accomplishes the need to measure and/or mark teeth easily and accurately so that braces can be correctly placed on the teeth in the ideal occluso-gingival position.

The invention provides a gauge with two arms. The first arm has two measuring axes. The first axis, (axis A) extends longitudinally along the long axis of the first arm and is used to measure the anterior teeth, i.e. the upper or lower cuspids and incisors. A vertical extension 38 is attached at a right angle to axis A and lies along an axis B, and the vertical extension 38 is typically rested on the mesial (the one closest to the front of the mouth) marginal ridge of a posterior tooth with axis A perpendicular to axis B and held parallel to the long axis of the tooth. The second arm of the gauge carries a pointed element, which may include an assortment of marking means, including but not limited to a pencil lead, washable inks delivered through a fine point, a grease pencil marker, or other known marking means or a non-marking means. The key element or measurement of the difference between axis A and the vertical tip of the axis B is approximately 2.5 mm with a variation of about 0.50 mm for most patients.

DETAILED DESCRIPTION OF THE INVENTION

Figure 1:
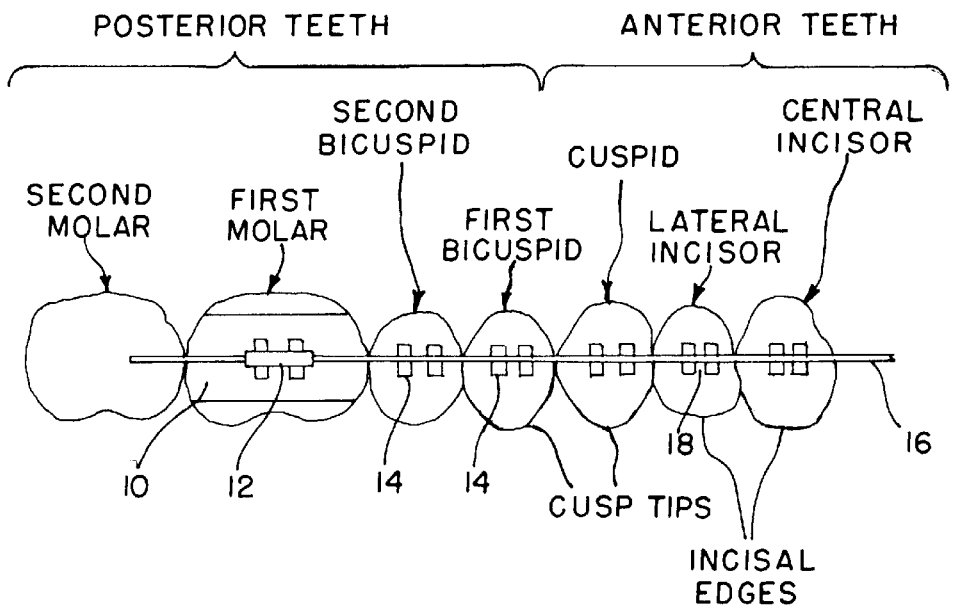
FIG. 1 is a cheek side view showing a quadrant of a patient's teeth with bands, brackets and an arch wire in the brackets.

FIG. 1 is a side view showing a quadrant of a patient's teeth (viz. the second molar, first molar, second bicuspid, first bicuspid, cuspid, lateral incisor, and central incisor) with bands 10 with molar tube 12 and brackets 14 mounted thereto. A segment of an archwire 16 is shown positioned in slots 18 of the brackets and in the molar tube 12. The teeth's incisal edges and cusp tips are shown.

Figure 2:
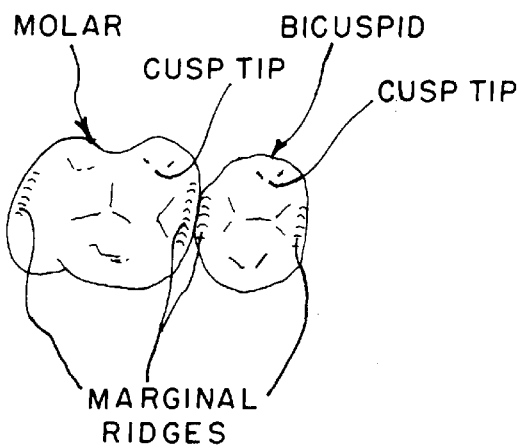
FIG. 2 is an occlusal (biting) surface view of the upper bicuspid and first molar.

FIG. 2 is a view of the upper bicuspid and first molar view from the occlusal (biting) surface showing the cusp tips and marginal ridges thereon.

Figure 3:
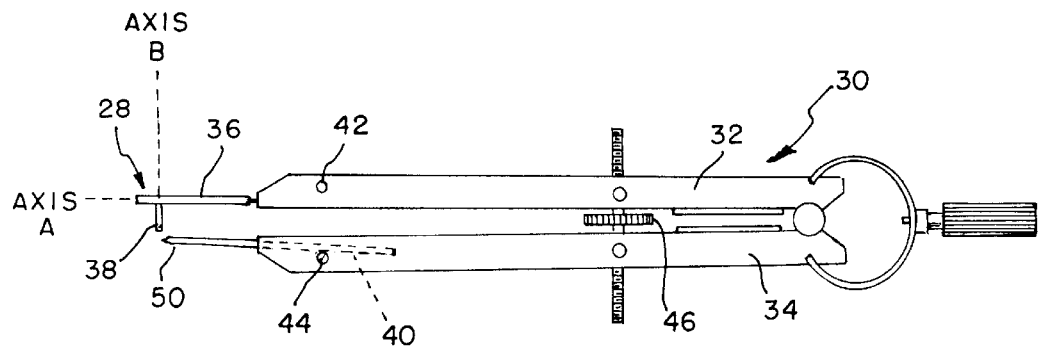
FIG. 3 is a side view of an embodiment of the gauge of the invention.

FIG. 3 is a side view of an embodiment of the gauge 30 of the invention. Gauge 30 has arms 32 and 34. Arm 32 has a gauge element 28 which has first longitudinal extension 36 which lies on a first axis A, and is used to measure the anterior teeth, i.e. the upper or lower cuspids and incisors. A vertical extension portion 38 is affixed to longitudinal extension 36 on a second axis, (axis B) which is preferably generally at a right angle to longitudinal extension 36 and axis A and is perpendicular to the opening and closing axes of the arms of the gauge. Vertical extension portion 36 is typically used by being rested on the mesial marginal ridge (the one closest to the front of the mouth) of a posterior tooth with axis A perpendicular to axis B held parallel to the long axis of the tooth. Second arm 34 of gauge carries a pointer element 40, which can be either a marking element, or a non-marking element. Marking element 40 can be chosen from any number of marking means, including but not limited to a pencil lead, washable inks delivered through a fine point, a grease pencil marker, or other known marking means, and non-marking element can be a metal scriber, for example. Pointed marker 40 has a pointed tip 50. Pointer element 40 (if in the form of an elongate pencil lead or an elongate scriber, for example) is preferably retained in second arm 34 in a position generally parallel to axis A of first arm 32. If the operator prefers a non-marking element, a pointed element may be used to measure the accuracy of the attachment placement. In order to provide for longitudinal adjustability of longitudinal extension 36 in first arm 32 and pointer element 40 in second arm 34, tension means 42 and 44 (e.g. thumbscrews) can be utilized. Although gauge 30 is shown in the general form of an arc drawing compass or bow divider with an adjustment knurl and screws 46 to (vary preferably continuously) the distance between the arms, the arms 32 and 34 could be set apart in a static and unadjustable orientation. Gauge element 28 can be provided as a separate part which can be used with standard dividing bows (which has been modified to provide for proper parallel orientation of the marking element (or non-marking element) and the gauge element on the arms) in place of the standard sharpened prong to convert standard dividing bows into gauges of the invention.

Figure 4:
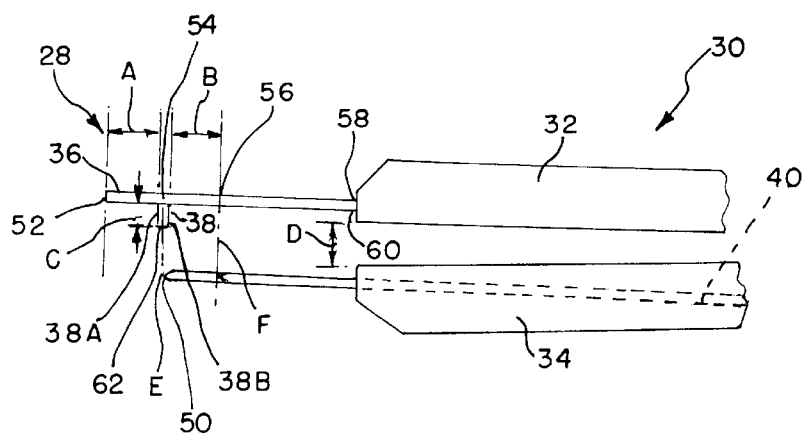
FIG. 4 is an enlarged view of the front end of the gauge of FIG. 3.

FIG. 4 is an enlarged view of the front end of the gauge 30 of FIG. 3. Longitudinal extension 36 has a tip 52, and vertical extension portion 38 extends from longitudinal extension 36. Vertical extension portion 38 has a length of about 2.5 mm with a variation of about plus or minus 0.50 mm for most patients. Longitudinal extension 36 preferably has a first visual guide mark 54, a second visual guide mark 56, and a third visual guide mark 58, all spaced apart from each other. Vertical extension 38 has a forwardly facing surface 38A and a rearwardly facing surface 38B. Vertical mark 58 is used as a guide to determine the degree to which it is inserted into first arm 32 to the degree to which it extends forwardly of a tip 60 of first arm 32. If the longitudinal extension is permanently affixed or unitary with first arm 32, no third marking 58 is needed. The visual guide marks are used as an aid to help position the point 50 of pointer element 40 in a forward or backward position, depending on whether anterior or posterior teeth are being measured and marked. The feature of the gauge to permit the marking element 40 to slide longitudinally forward and backward in arm 34 provides a function so that when the gauge is first positioned on the tooth to be measured the marker may slide forward to place the mark on the tooth at the correct place. Tip 52 is distance A away from vertical extensionp's forwardly facing surface 38A and vertical extension's rearwardly facing surface 38B is spaced distance B from the rearwardly lying second guide mark 56. Distances A and B are preferably about 3 mm plus or minus 1.0 mm and is ideal for most patients. First and second arms 32 and 34 are preferably spaced apart a sufficient distance D such as to provide for the required spacings of the arms so that longitudinal extension 36 and pointer element 40 are preferably parallel or close to parallel. This necessitates modifying a typical bow divides to achieve this parallelism. The projection of tip 50 of pointer element 40 can be adjusted to abut a vertical projection line E from the centerline of vertical extension 38 and first guide mark 54 or to abut a vertical projection line F projecting vertically downwardly from second guide mark 56. In either case, vertical extension 38 has a distal tip 62 that is spaced apart from marking element 40.

Figure 5:
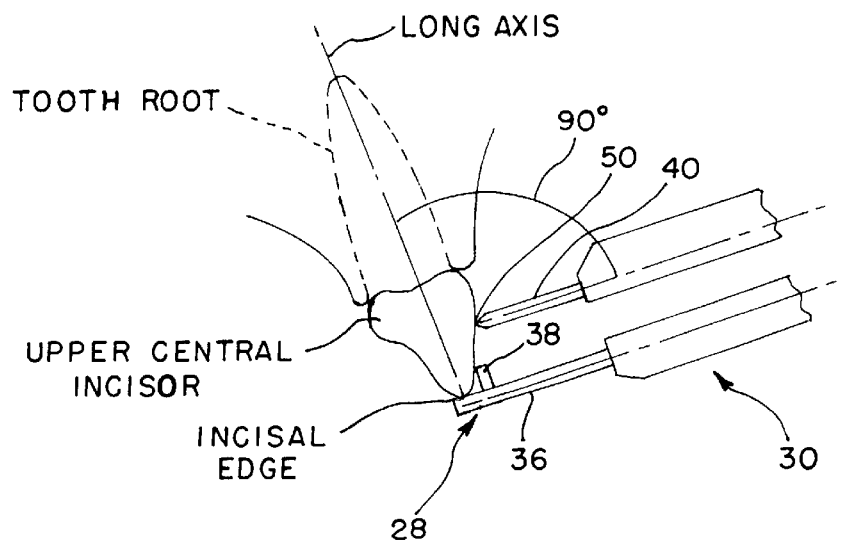
FIG. 5 is an interproximal view of the upper central incisor with the gauge of FIG. 3 in place.

The use of the gauge is best described with reference to FIGS. 5 and 6. The operator first determines on a selected tooth (typically a first molar) where the attachment should be ideally positioned. The user uses gauge 30 to measure the correct vertical distance to position the tube or slot of the bracket on the tooth. On lower teeth, the attachments should be placed low enough on the buccal surface of the clinical crown toward the gingival, to avoid traumatic occlusion, i.e. upper teeth striking the attachment before full closure and contact of opposing teeth are effected. On the upper teeth, the attachments are usually positioned near the center of the typical clinical crown occluso-gingivally. For use in marking an upper tooth, (e.g. an upper central incisor), as shown in FIG. 5, the user will place longitudinal extension 36 so that it rests on the incisal edge of the upper central incisor with vertical extension 38 resting on a front of the tooth. With the axis A of longitudinal extension 36 at a right angle (or generally right angle) to a long axis of the tooth (with axis B of vertical extension 38 being parallel or generally parallel thereto, tip 50 of pointer marking element 40 (if it is a marker element) is used to mark the interproximal surface (front) of the tooth.

Figure 6:
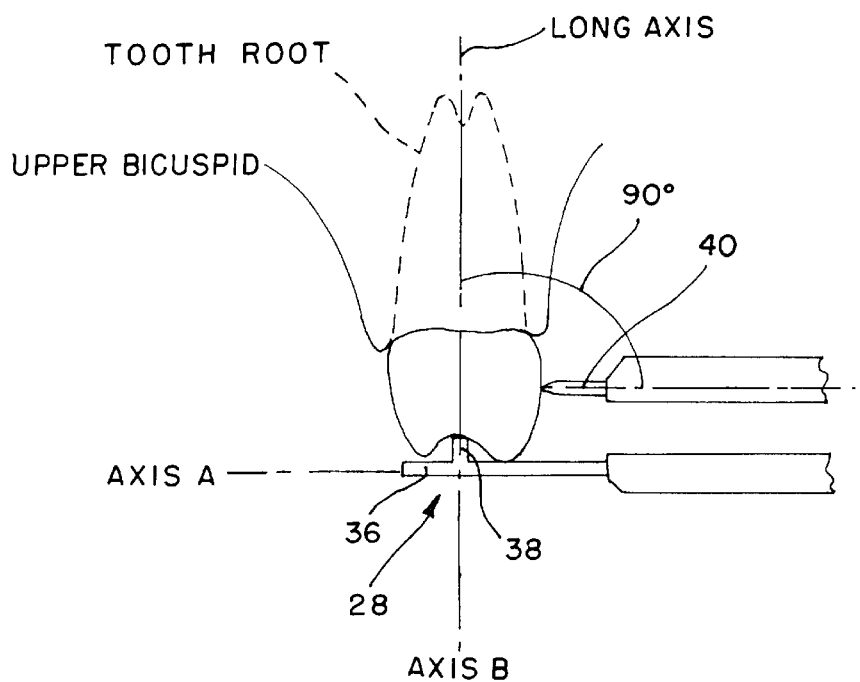
FIG. 6 is an interproximal view of the upper bicuspid with the gauge of FIG. 3 in place.

Once the gauge is set at the correct height for the attachments to be placed, for example on the upper teeth, it remains set at that height while all the teeth of the upper arch are measured and marked, as shown in FIGS. 5 and 6. The mark is placed near the interproximal of each tooth so that the attachment may be affixed to the tooth using the mark as a reference guide. In the case of marking a bicuspid, FIG. 6 shows the use of the gauge to mark an upper bicuspid, wherein vertical extension 38 is placed in contact with the marginal ridges and is held with its axis B held generally parallel to the long axis of the tooth, and with the longitudinal extension 36 and its axis A generally perpendicular to the long axis of the tooth. Held as such, pointed tip 50 of marking element 40 can be used to place a mark on the face of the tooth.

Figure 7:
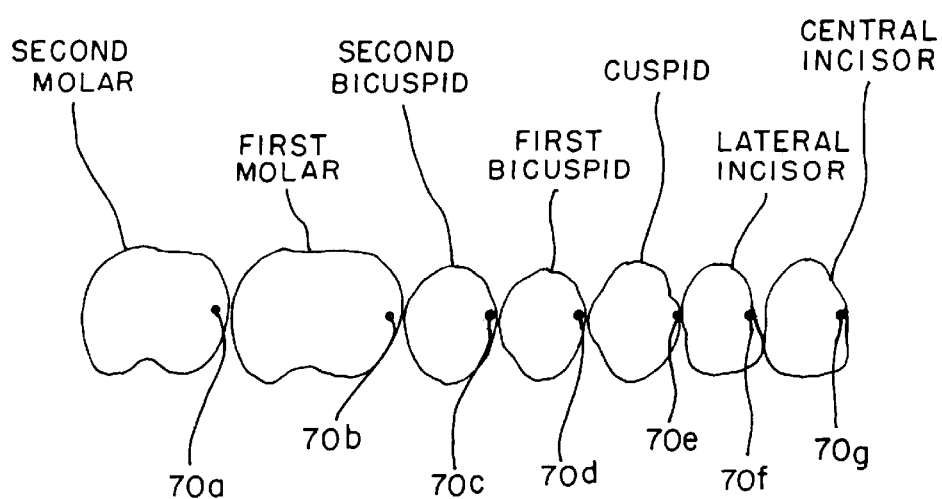
FIG. 7 is a side view of the buccal and labial surfaces of the upper right quadrant of a patient teeth, with marks made by the gauge.

FIG. 7 shows the teeth to which bands or brackets will be attached thereto after being marked with marks 70a, 70b, 70c . . . 70g. The marks thus made are not covered at this time by the attachments and serves as a constant guide for placement. In certain situations, the interproximal gingival papilla may be marked instead of the tooth and may be used as the reference mark. When the operator wishes to set the height of the attachments for the lower teeth, it may be at a different height setting than the upper, but as in the case of the example of marking the upper teeth, remains the same setting while the lower teeth are marked.

Figure 8:
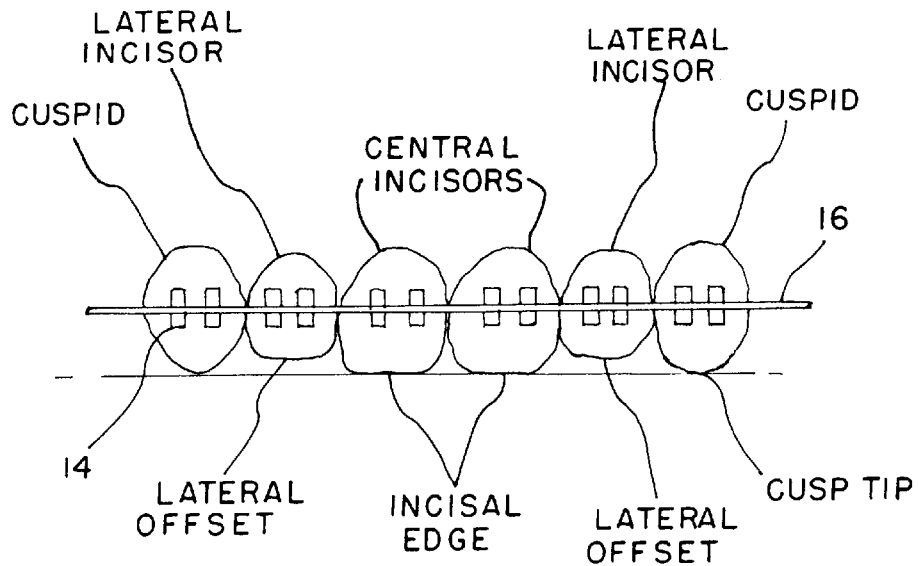
FIG. 8 is a front view of a patient's mouth from the lip side showing six upper anterior teeth with attachments mounted to the teeth and a straight archwire segment.
Figure 9:
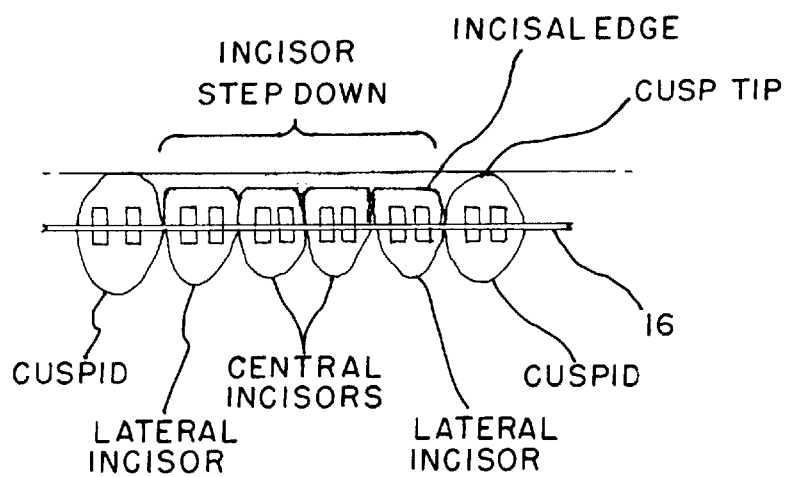
FIG. 9 is a front view of a patient's mouth from the lip side showing six lower anterior teeth with attachments mounted to the teeth and a straight archwire segment.

Due to anatomic variations and functional characteristics of the upper and lower front teeth, slight adjustments of the vertically marked positions by the gauge may be necessary. Indeed, regarding the upper anterior teeth, the position set and marked by the gauge is used to position the cuspids and central incisors. The lateral incisors typically need to be offset by one half to one millimeter. Offset means that the incisal edges of the lateral incisors are placed one half to one millimeter toward the gingival from a line passing through the central incisal edges and the cuspid tips, which is shown in FIG. 8. To do this, the mark originally placed on the lateral incisors when the gauge is used, is moved one half to one millimeter closer to the incisal edge of these teeth. The effect, when a straight wire is passed though the bracket slots of the upper six anterior teeth, is to offset or raise the lateral incisors relative to the cuspids and central incisors and ideally position these lateral incisors both cosmetically and functionally. With regards to the lower anterior teeth, the gauge position set and marked for the lower arch is used in the anterior for the cuspids only. All four lower incisors typically need to be stepped down (gingivally) approximately one half to one millimeter, as shown in FIG. 9. To do this, the mark originally placed on the four incisors is moved incisally, away from the gingival approximately one half to one millimeter. The net affect positions the lower anterior teeth ideally, both cosmetically and functionally.

To reiterate, this gauge is unique in that once set for a particular arch, it measures the height for placement of an attachment on each tooth in relation to the edges of the anterior teeth with adjustments to these teeth previously described. That same measurement is in harmony with the correctly marked height of the posterior teeth, with the marginal ridges as a measurement point, (using the tip of axis B) and the opposing marking element of the gauge to mark the teeth.

The marking system of the gauge is also unique in that it leaves a very small mark or dot near the interproximal surface of the tooth at the correct height for placement of a given attachment when the pointer element is a marker element. This mark is preferably off center near the interproximal, so that an attachment may be attached to a tooth without covering the mark, thus serving as a constant guide in placing the attachment at the correct height. This feature alleviates the need to use a gauge a second time to check attachment position before the attachment is fixed in position. Where the pointer element is just used for measurement, the place where the tip of the pointer element rests on the tooth can be used to adjust the position of the brackets placed on the tooth.

The gauge of the invention preferably also has a continuous range of settings to adjust the distance between axis A of longitudinal extension 36 and tip 50 pointer element 40, since the gauge can have a general form of an arc drawing bow divider, with adjustment knurl and screws 46 serving this function (as shown in FIG. 3). In contrast, currently used gauges have three to four measurement heights that are fixed and not adjustable. Furthermore, these current gauges use the cusp tips of the posterior teeth rather than the marginal ridges as reference measuring points and have no marking capability. An added refinement to the gauge is to make the marking member able to slide forward and backward so that the gauge is first positioned on the tooth to be measured and the marker slides forward to place the mark on the tooth at the correct place.

The dual axis principal of the gauge could also be used in gauges designed to measure correct placement heights for attachments that are fitted to models of a given patient's teeth for indirect placement of attachments on teeth. In this indirect mode, models are made of the teeth of a given patient and attachments are placed ideally on the models versus on the teeth of the patient. Through an impression made of the model with attachments placed thereon, the attachments can then be transferred in this impression to the actual teeth of the patient and permanently attached, for example, a quadrant of the mouth at a time. Such a method might be used for rapid attachment of the brackets to the patient's teeth.

Having thus described the invention, it should be apparent that numerous structural modifications and adaptations may be resorted to without departing from the scope and fair meaning of the instant invention as set forth hereinabove and as described hereinbelow by the claims.

What is claimed is:

1. A gauge for marking teeth or models of teeth for the determination of the placement of attachments for orthodontic braces, comprising:
   a first arm with a gauge element comprising a longitudinal extension portion lying on a first axis and a vertical extension portion extending generally perpendicularly from the first axis of the longitudinal extension portion;
   a second arm which has a pointer element at an end thereof, the pointer element having a tip which is spaced apart from the longitudinal extension portion of the first arm, the first and second arm being connected together to maintain the spaced apart relationship between the tip of pointer element and the longitudinal extension portion with the vertical extension portion extending towards the pointer element;
   said longitudinal extension portion having a distal end and said vertical extension portion being spaced from said distal end;
   said vertical extension being disposed substantially in coincidence with an imaginary plane intersecting said first and second arms.

2. The gauge of claim 1, wherein the first and second arms are moveably connected together to permit adjustment of the spacing between the first and second arms.

3. The gauge of claim 1, wherein the first and second arms are moveably connected together in the form of a dividing bow.

4. The gauge of claim 1, wherein the vertical extension portion extends outwardly between about 2.00 mm and 3.00 mm from the longitudinal extension portion.

5. The gauge of claim 1, wherein the longitudinal extension portion of the gauge element is longitudinally moveable relative to the first arm portion.

6. The gauge of claim 1, wherein the pointer element is longitudinally moveable relative to the first arm portion.

7. The gauge of claim 1, wherein the pointer element is a marker element selected from the group consisting of at least one or more of a pencil lead, an ink marker, and a grease pencil lead.

8. The gauge of claim 1, wherein the longitudinal extension portion and the pointer element are maintained in a generally parallel relationship in the gauge.

9. The gauge of claim 1, wherein the longitudinal extension portion has at least one visible guide mark formed thereon between a position where the vertical extension portion extends from the longitudinal extension portion and a portion of the longitudinal extension portion which extends from the first arm.

10. The gauge of claim 1, wherein the vertical extension portion is spaced about 3 mm plus or minus 1.0 mm from a distal tip of the longitudinal extension portion.

11. A gauge for marking teeth or models of teeth for the determination of the placement of attachments for orthodontic braces utilizing the anterior of said teeth having incisal edges and the posterior of said teeth having marginal ridges, comprising:
    a first arm with a longitudinal extension portion lying on a first axis, a vertical extension portion extending generally perpendicularly from the first axis of the longitudinal extension portion with the vertical extension portion extending outwardly substantially 2.5 mm from the longitudinal extension portion;
    a second arm which has a marking element at an end thereof, the marking element having a tip which is spaced apart from the longitudinal extension portion of the first arm and with the vertical extension portion extending towards the marking element, the first and second arm being moveably connected together to permit adjustment of the spacing between the first and second arms;
    said longitudinal extension being adapted to abut said incisal edges and the free end of said vertical extension being adapted to abut said marginal ridges.

12. The gauge of claim 11, wherein the longitudinal extension portion of the gauge element is longitudinally moveable relative to the first arm portion.

13. The gauge of claim 11, wherein the marking element is longitudinally moveable relative to the first arm portion.

14. The gauge of claim 11, wherein the marking element is selected from the group consisting of at least one or more of a pencil lead, an ink marker, and a grease pencil lead.

15. The gauge of claim 11, wherein the longitudinal extension portion and the marking element are maintained in a generally parallel relationship in the gauge.

16. The gauge of claim 11, wherein the longitudinal extension portion has at least one visible guide mark formed thereon between a position where the vertical extension portion extends from the longitudinal extension portion and a portion of the longitudinal extension portion which extends from the first arm.

17. A gauge for marking teeth or models of teeth for the determination of the placement of attachments for orthodontic braces, comprising:

a first arm with a longitudinal extension portion lying on a first axis, a vertical extension portion extending generally perpendicularly from the first axis of the longitudinal extension portion with the vertical extension portion extending outwardly between about 2.00 mm and 3.00 mm from the longitudinal extension portion;

a second arm which has a marking element at an end thereof, the marking element having a tip which is spaced apart from the longitudinal extension portion of the first arm and with the vertical extension portion extending towards the marking element, the first and second arm being moveably connected together to permit adjustment of the spacing between the first and second arms, and said longitudinal extension portion of the gauge element being longitudinally moveable relative to the first arm portion.

18. The gauge of claim 17, wherein the longitudinal extension portion and the marking element are maintained in a generally parallel relationship in the gauge.

19. The gauge of claim 17, wherein the longitudinal extension portion has at least one visible guide mark formed thereon between a position where the vertical extension portion extends from the longitudinal extension portion and a portion of the longitudinal extension portion which extends from the first arm.

20. A method of marking teeth or models of teeth comprising the steps of spacing the two arms of a gauge a desired distance apart, placing one arm in abutment with the incisal edges of the anterior teeth in one arch, marking said anterior teeth with the other of said arms, placing the tip of a vertical extension extending generally perpendicular from said one arm on the marginal ridges of the posterior teeth of said arch, and marking said posterior teeth with said other arm.

21. A method of making teeth or models of teeth comprising the steps of spacing the two arms of a gauge a desired distance apart, placing the tip of a vertical extension extending generally perpendicular from one arm on the marginal ridges of the posterior teeth in one arch, and marking said posterior teeth with the other of said arms, placing said one arm in abutment with the incisal edges of the anterior teeth in once arch, and marking said anterior teeth with said other arm.

22. A gauge for making teeth or models of teeth for the determination of the placement of attachments for orthodontic braces, comprising:

a first arm with a longitudinal extension portion lying on a first axis, a vertical extension portion extending generally perpendicularly from the first axis of the longitudinal extension portion with the vertical extension portion extending outwardly between about 2.00 mm and 3.00 mm from the longitudinal extension portion;

a second arm which has a marking element at an end thereof, the marking element having a tip which is spaced apart from the longitudinal extension portion of the first arm and with the vertical extension portion extending towards the marking element, the first and second arm being moveably connected together to permit adjustment of the spacing between the first and second arms;

and said longitudinal extension portion and said marking element being maintained in a generally parallel relationship in the gauge.

23. A gauge for marking teeth or models of teeth for the determination of the placement of attachments for orthodontic braces, comprising:

a first arm with a longitudinal extension portion lying on a first axis, a vertical extension portion extending generally perpendicularly from the first axis of the longitudinal extension portion with the vertical extension portion extending outwardly between about 2.00 mm and 3.00 mm from the longitudinal extension portion;

a second arm which has a marking element at an end thereof, the marking element having a tip which is spaced apart from the longitudinal extension portion of the first arm and with the vertical extension portion extending towards the marking element, the first and second arm being moveably connected together to permit adjustment of the spacing between the first and second arms;

and said longitudinal extension portion having at least one visible guide mark formed thereon between a position where said vertical extension portion extends from said longitudinal extension portion and a portion of said longitudinal extension portion which extends from said first arm.

\* \* \* \* \*